United States Patent [19]

Shamp

[11] Patent Number: 4,988,360
[45] Date of Patent: Jan. 29, 1991

[54] ARTICLE AND METHOD FOR FITTING A PROSTHETIC, ISCHIAL CONTAINMENT SOCKET TO AN ABOVE-KNEE AMPUTEE

[75] Inventor: Daniel L. Shamp, Akron, Ohio

[73] Assignee: Prosthetic Consultants, Inc., Akron, Ohio

[21] Appl. No.: 465,021

[22] Filed: Jan. 16, 1990

Related U.S. Application Data

[62] Division of Ser. No. 226,128, Jul. 29, 1988, Pat. No. 4,921,502.

[51] Int. Cl.$^5$ ............................. A61F 2/80; A61F 2/76
[52] U.S. Cl. ......................................... 623/33; 623/36
[58] Field of Search ...................................... 623/33–38

[56] References Cited

U.S. PATENT DOCUMENTS

| | | |
|---|---|---|
| 1,216,367 | 2/1917 | Rowley . |
| 3,889,301 | 6/1975 | Bonner, Sr. . |
| 4,161,042 | 7/1979 | Cottingham et al. ................. 623/33 |
| 4,300,245 | 11/1981 | Saunders . |
| 4,735,754 | 4/1988 | Buckner ........................... 623/27 X |
| 4,872,879 | 10/1989 | Shamp .................................. 623/36 |
| 4,921,502 | 5/1990 | Shamp .................................. 623/33 |

FOREIGN PATENT DOCUMENTS

| | | | |
|---|---|---|---|
| 2586555 | 3/1987 | France ................................. 623/33 |
| 2103490 | 8/1981 | United Kingdom .................. 623/33 |
| 2098488 | 11/1982 | United Kingdom .................. 623/33 |

Primary Examiner—Randall L. Green
Assistant Examiner—David H. Willse
Attorney, Agent, or Firm—Renner, Kenner, Grieve, Bobak, Taylor & Weber

[57] ABSTRACT

An interface fitting module (10) for fitting the interface portion of an ischial containment socket for an above-knee amputee. The module (10) has a sleeve-like body portion (11) with proximal and distal ends (12 and 13), respectively. At least the proximal end (12) of the body portion (11) is open to receive the residual thigh (15) of an above-knee amputee. Means in the nature of a lap joint (25) are provided selectively to adjust the peripheral dimension of said body portion (11) so that it will circumscribe, and engage, the peripheral thigh (15) to the desired degree. The body portion (11) of the module (10) is sufficiently transparent to permit visual observation as to the conformity between the body portion (1) of the module (10) and the residual thigh (15) received therein. The body portion (11) is made from a material, such as thermoplastic polymeric material, which may be selectively modelled to effect localized conformity of the body portion (11) to the configuration of the residual thigh (15) received within the module (10).

4 Claims, 3 Drawing Sheets

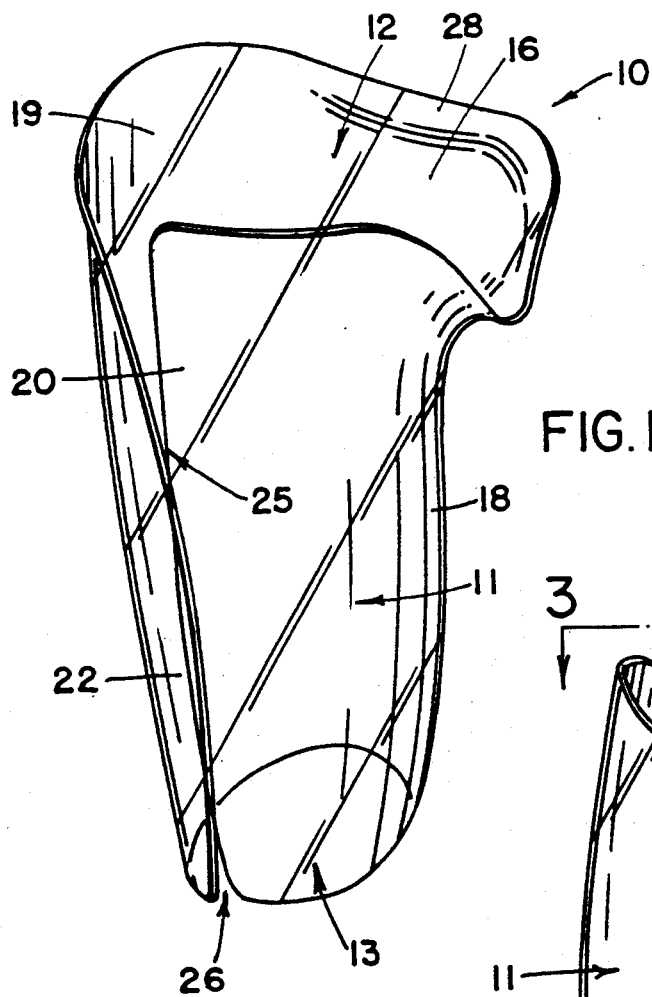
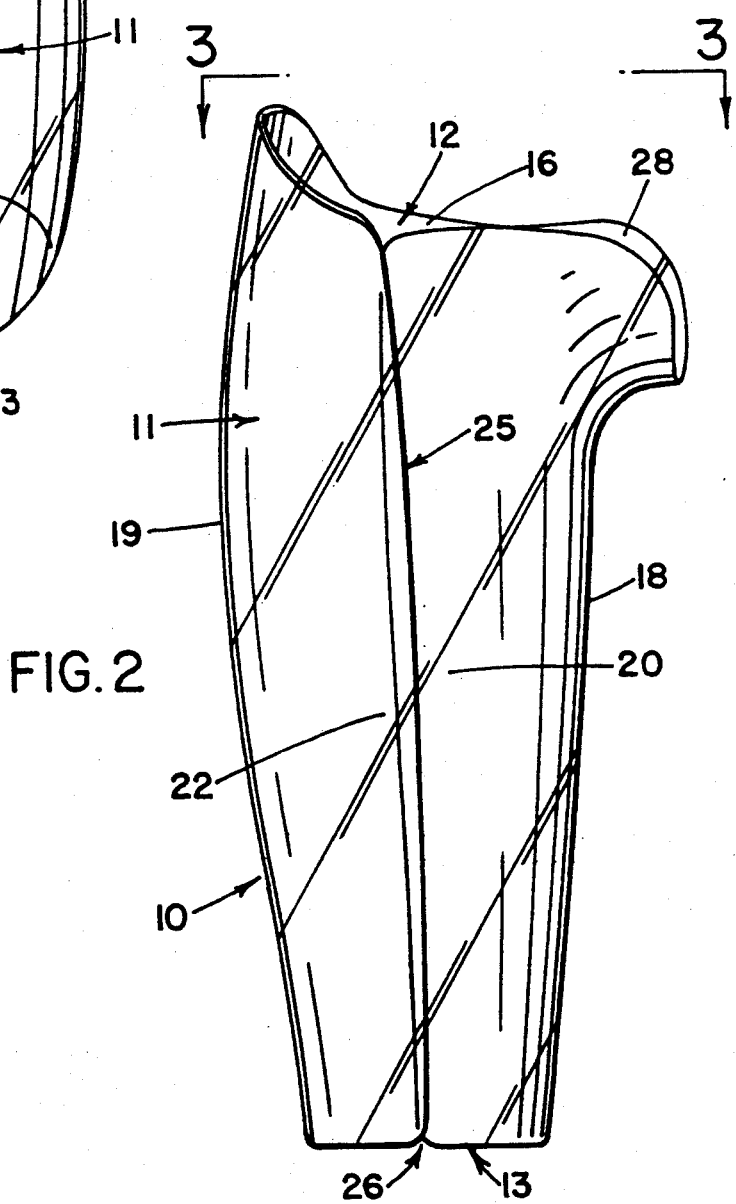

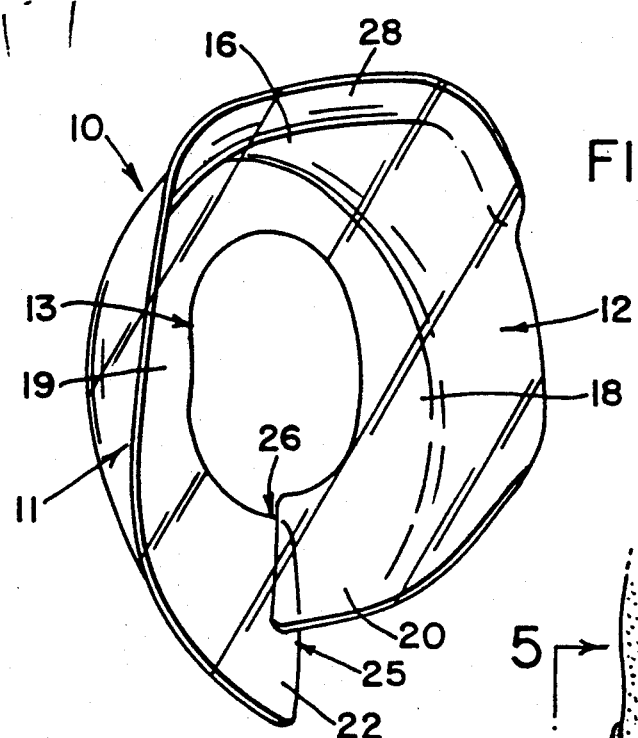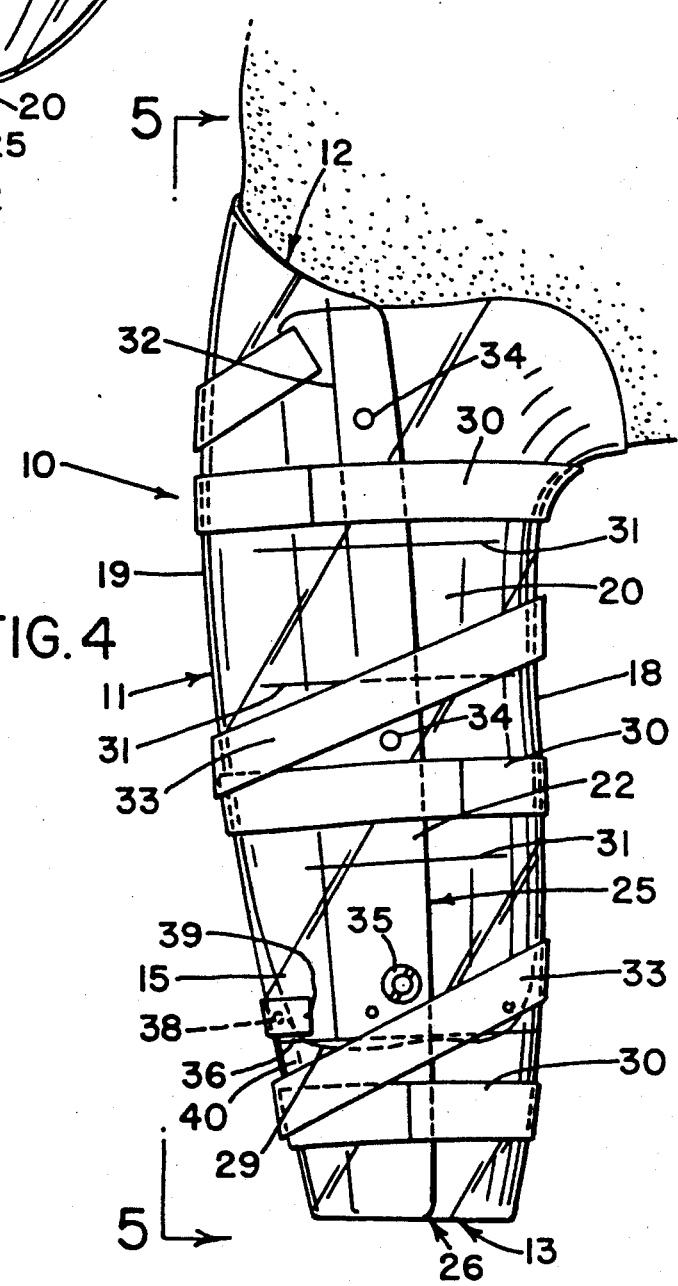

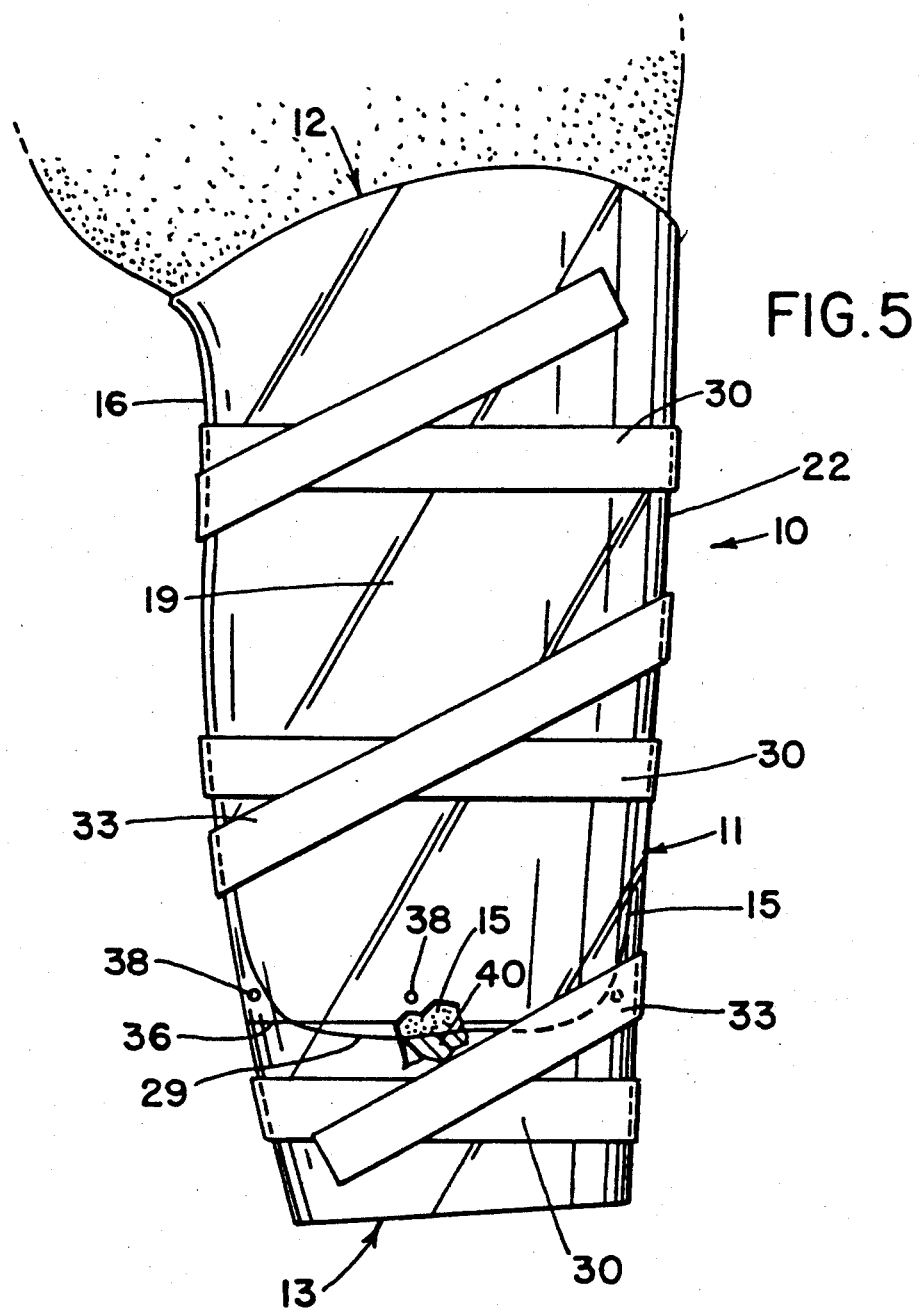

ARTICLE AND METHOD FOR FITTING A PROSTHETIC, ISCHIAL CONTAINMENT SOCKET TO AN ABOVE-KNEE AMPUTEE

This application is a division of application Ser. No. 226,128, filed July 29, 1988, now U.S. Pat. No. 4,921,502, issued on May 1, 1990.

TECHNICAL FIELD

The present invention relates generally to prosthetic socket arrangements employed to secure an artificial limb to the residual thigh of an above-knee amputee. More particularly, the present invention relates to an article, and method, for fitting a prosthetic socket utilized to secure an artificial limb to the residual thigh of an above-knee amputee. Specifically, the present invention relates to the configuration, and use, of a circumferentially adjustable and a deformably shapeable interface fitting module which can be accurately, and conveniently, fitted to a residual thigh in order to provide an exact negative mold of the residual limb from which the actual interface for a prosthetic socket can itself be fabricated.

BACKGROUND OF THE INVENTION

In the late 1940s the quadrilateral socket was introduced to the United States, and during the intervening years since its introduction the "quad socket" has been the standard design for fitting a prosthetic limb to the residual thigh of an above-knee amputee. During the approximately 40 years in which the quad socket has been employed in the United States it has become clear, however, that there are certain problems, particularly as to comfort and stability, inherent to the use of the quad socket.

Although there are many variations to the quad socket, it consistently presents a horizontally oriented brim at the proximal posterior. The horizontal brim serves as the ischial seat upon which the user's ischial tuberosity is supported. In fact, that portion of the user's weight which would normally have been supported by the amputated limb is transferred to the quad socket through the ischial seat.

The geometry of the quad socket purposely provides a rather narrow dimension, measured from the anterior to the posterior wall of the socket, in relation to the medial/lateral dimension. The aforesaid dimensional relationship of the quad socket was selected to assure that the socket applies pressure on the anterior of the residual thigh to push the ischium toward the posterior of the socket in order that the ischial tuberosity will be forced to rest solidly on the ischial seat presented by the brim at the proximal posterior of the socket. To accommodate the compression of the thigh which results within the quad socket because of the purposely narrowed anterior/posterior dimension, the medial/lateral dimension of the socket is made relatively larger.

However, the enlarged medial/lateral dimension makes it virtually impossible to provide sufficient lateral support for the distal end of the femur in the residual limb, as would be required to eliminate a limp during that portion of the user's gait when the artificial limb is in the weight bearing mode and the sound leg is swinging through to the next step. In fact, many knowledgeable commentators are of the opinion that the quad socket is ineffective in all but the mid-stance phase of the gait due to the excessive abduction of the femur permitted within the quad socket because of the aforesaid dimensional relationship.

Recognition of the deficiencies inherent to the quad socket is, in effect, a challenge to the basic concept that the ischial tuberosity should serve to transmit the majority of the weight expected to be carried by the residual limb to the ischial seat provided for that purpose on the quad socket. Such a challenge recognizes that the structural arrangement of the quad socket has the basic inability to stabilize the femur when the gluteus medius fires; the arrangement of the quad socket, after all, provides no structure whereby the ischium is able to preclude abduction of the femur. It is this inability to stabilize the femur which results in the necessity for the user to lean laterally in an attempt to stabilize the pelvis, thus presenting the readily recognizable limp required of a person using the quad socket.

Specifically, as the gluteus medius pulls the femur into abduction, the pelvis slides medially because the ischial tuberosity is free to shift along the ischial seat of the quad socket; The unsupported femur has little choice but to abduct in a more pronounced attitude within the wide medial/lateral dimension of the quad socket. The pronounced abduction imposes pain at the distal end of the femur as well as at the proximal medial portion thereof. To reduce the undesirable pressure, and the resulting pain, the patient leans to position the torso over the abducted, distal end of the femur.

The aforesaid negative characteristics of the quad socket can be obviated by a much more recent innovation in prosthetic sockets which employs a narrower medial/lateral dimension and a wider anterior/posterior dimension, the relative dimensions being chosen such that the ischial tuberosity and a portion of the ramus of the ischium is contained within the socket. The recently developed, narrow medial/lateral socket configuration also employs a relatively high lateral wall which provides medially directed reactive forces proximal and distal to the greater trochanter. In this arrangement the abduction angle of the femur in the residual limb more closely approaches that of the femur in the sound extremity during all portions of the user's gait, thus greatly reducing the characteristic limp.

This recently developed socket design is not, however, designated by a universally accepted appellation. At present such a socket design is designated as a "N.S.N.A. (*N*ormal *S*hape *N*ormal *A*lignment) socket," or a "narrow ML (*M*edial/*L*ateral) socket" or a "Cat-Cam (*C*ontoured, *A*dducted *T*rochanteric, *C*ontrolled, *A*ligned *M*ethod) socket." The most recent improvement of an ischial containment socket which has the desired, relatively narrow, medial/lateral dimension is disclosed and claimed in my copending U.S. patent application Ser. No. 099,778, filed on Sept. 22, 1987, now U.S. Pat. No. 4,872,879. Irrespective of the name employed, in order to provide an effective socket which incorporates the narrow medial/lateral dimension a more precise fitting of the socket to each patient is normally required for the narrow medial/lateral socket, as are multiple tests of the socket prior to fabrication of the finished prosthetic limb. Nevertheless, the greater comfort and the improved functionality that can be achieved by this new design has been thought to offset the inconvenience, and increased cost, at least to those who can afford both the time and expense.

Except when using the prefabricated interface unit disclosed in the aforesaid U.S. Pat. No. 4,872,879, to fabricate either the historic quad socket or the more recently developed, narrow medial/lateral socket, the prosthetist employs a negative model of the amputee's residual thigh. To assure comfort to the user, it is necessary that the negative model comfortably contain the residual limb and reflect the position assumed by the residual limb when it is bearing the amputee's weight. The load bearing disposition of the residual limb constitutes the condition when the residual limb and the prosthesis are subjected to the most stress and are most likely to cause discomfort to the amputee. Therefore, the prosthetist attempts to fabricate the interface portion of the socket such that it will provide the maximum support during the weight bearing mode.

Heretofore negative castings of the residual limb in its weight bearing disposition have been made by casting a plaster mold of the thigh while the amputee is standing with his limb in a casting brim. A casting brim incorporates a number of individual pads which can be separately adjusted to engage the residual limb in a manner which attempts to mimic a prosthetic socket and thereby provide maximum support to the residual limb of the individual patient.

Once the several pads of the casting brim are disposed in what the prosthetist deems to be the most appropriate arrangement to mimic a prosthetic socket for the individual patient, the patient then removes his limb from the brim. A plaster casting material is interposed between the casting brim and the residual limb in such a way that it fully encapsulates the residual limb. When the casting material has hardened it comprises a negative model of the residual thigh in the weight bearing position, and that negative model is used in the production of a positive reproduction of the residual limb to which the interface portion of the prosthetic socket is fitted.

In order to assure comfort to the patient, and to accommodate the bio-mechanics occasioned by the interaction between the residual limb and the prosthetic socket, the primary, technical objective of the interface is to maintain the femur of the residual limb in an attitude comparable to the disposition of the femur in the sound leg. This can become quite complicated as the prosthetist seeks to fabricate a comfortable interface, and particularly when using many of the brim casting techniques employed in fitting quadrilateral sockets.

A brief description of one of the more successful brim casting techniques for fitting the narrow, medial/lateral socket (which technique has a satisfactorily easy learning curve for the prosthetist and provides consistently positive results for the patient) will immediately substantiate the considerable improvement which results from the use of an interface fitting module embodying the concepts of the present invention. The typical brim casting technique requires several accurate measurements. First, the circumference of the residual limb is measured at approximately two inch (2.54 cm) increments along the length of the residual limb. The length of the residual limb, measured from the ischial tuberosity, must be known, and three unique medial/lateral measurements, and a rather different anterior/posterior measurement, must be precisely taken. The medial/lateral measurements are taken, as follows:

1. A firm medial/lateral measurement must be taken one to two inches distal to the ischium. This measurement is referred to as the *D*istal *I*schial *T*uberosity measurement—i.e., the DIT—and is taken with large caliper pads so as not to over compress the flesh of the residual limb in a medial/lateral direction.

2. A firm medial/lateral measurement must be taken from the medial side of the ramus of the tuberosity to a point just superior to the greater trochanter of the femur. This measurement is referred to as the *O*blique medial/lateral dimension—i.e., the OB—and is a bony measurement which may be taken firmly.

3. A firm medial/lateral measurement is also a bony measurement which may be taken firmly from the medial border of the ramus of the ischium to the subtrochanteric area of the femur. If the ischial tuberosity is palpated, the prosthetist will find that the measurement is actually taken from an area superior and medial to the ischial tuberosity. This measurement is referred to as the ischial tuberosity *M*edial/*L*ateral—i.e., the ML.

An anterior/posterior measurement is also taken, but the manner in which the measurement is taken differs from the anterior/posterior measurement taken for fitting a quadrilateral socket in that it is a "surface tight," or silhouette, measurement taken with the medial/lateral flesh firmly compressed. With the residual limb compressed in a medial/lateral direction the anterior/posterior dimension is slightly elongated, and it is the elongated anterior/posterior dimension which is measured. Finally, the femoral adduction angle is measured with the patient holding the limbs as though the knees were pressed together into tight adduction with the pelvis.

The pads of the brim are then selectively positioned in a brim stand in conformity with the aforesaid measurements. In brief, the procedure entails:

1. Levelling the pad which constitutes the posterior wall of the brim.
2. Orienting the medial and lateral pads of the brim such that they are disposed at a declining angle (on the order of 10° to 20°) from the lateral to the medial wall. This is necessary for the ischial tuberosity to be contained within the socket and for the pubic ramus to remain out of the socket.
3. Setting the adduction angle on the lateral bar of the brim into conformity with that angle, as measured on the patient.
4. Setting the DIT as measured from the patient, plus approximately ¼ inch (0.635 mm) to accommodate the thickness of the plaster, on the lateral pad.
5. Checking to be certain that the medial and lateral walls are not parallel but are wider anteriorly in the region of the adductor longus.
6. Positioning the oblique pad so that it will firmly press against the patient proximal to the trochanter with the posterior portion engaging the posterior of the residual thigh at the mid medial/lateral point. The oblique pad should parallel the wing of the ilium.
7. Positioning the anterior pad to the dimension of the patient plus approximately ¼ inch (0.635 mm), to accommodate the thickness of the plaster.
8. Establishing the circumferential measurement, defined by the brim pad locations, in conformity with the circumferential measurements of the patient's residual limb—plus approximately one inch (2.54 cm) to accommodate the thickness of the plaster.
9. Because this procedure forms a weight bearing cast, the evaluation performed at this step is critical. That is, the procedure continues by palpating the patient's residual limb to assure that: the ischium will be contained within the socket; the pubic ramus lightly touches the medial wall; the lateral pad firmly contacts the patient; and, the femur is centralized within the flesh of the residual limb. During this evaluation the patient wears a five ply stocking to simulate the plaster wraps subsequently applied to form the negative impression casting.

10. Readjusting the oblique pad snugly to rest against the patient's side.
11. Checking to determine that the ischium is received approximately ½ to ¾ inch (1.270 mm to 1.905 mm) within the socket—too great a depth applies pressure to the coccyx, blocking hip extension. A full range of hip motion is required; adduction or extension must not be blocked.

With the components of the brim thus properly disposed, the brim is prepared by applying, and smoothing, plaster splints to the medial and posterior surfaces of the brim in order to assure accurate copying of the brim contour. The patient is prepared by applying approximately two layers of an elastic plaster wrap over the thin stockinet which shields the patient's residual limb, and thereafter applying approximately two additional layers of a rigid plaster wrap. Preparation of the residual limb is concluded by applying a plaster splint against the proximal trochanteric region which is held firmly in position by the oblique pad. Particular care is taken to provide cover high on the lateral side of the hip, at least to the level of the iliac crest.

After concluding the aforesaid pre-preparation, the patient inserts the covered, residual limb into the brim fixture. The pubis should lightly contact the medial wall of the brim to assure that the residual thigh has been inserted into the brim to the proper depth. The patient then forcefully adducts the residual limb.

If the measurements have been accurately taken, and properly transferred to the brim, the brim will form the proximal socket shape while the prosthetist directs his, or her, attention to the distal aspect of the residual limb. One hand is employed to centralize the femur within the tissue of the residual limb by pulling the distal medial tissue in a lateral direction. The other hand is used to create an angular disposition to the distal, lateral area of the residual limb in order to stabilize the femur and protect the distal end of the residual limb. When the plaster has completely hardened, the brim is lowered and the patient removes the residual limb from the resulting negative casting.

However, even with careful attention to detail while performing the most widely accepted of the prior known interface fitting techniques, it is impossible to assure that a completely satisfactory interface has been fabricated prior to actual use of a socket which incorporates the resulting interface. Thus, it has heretofore been generally required that a plurality of check sockets be made before finalizing the fitting.

Hence, while a plaster cast of the residual limb can provide a highly accurate and effective model for use in fabricating a quad socket, the process often proves time consuming and expensive. Numerous adjustments are often required properly to position the casting brim before the casting can be made. Moreover, the casting process is itself quite involved and requires close attention to detail. Unfortunately, if the casting proves to be improper, the entire process must be repeated.

In addition, the disposition of the residual limb within the casting brim may be such that the limb is unduly flattened against, or too loosely engaging, one of the adjustable brim pads, and the prosthetist can not always determine that situation until the model is completed, or worse, until the patient tries the resulting socket.

SUMMARY OF THE INVENTION

It is, therefore, a primary object of the present invention to provide an improved article and method by which to fit the interface of a prosthetic socket for securing an artificial limb to the residual limb of an above-knee amputation, the improved article being as well adapted to the fitting of an interface for use in conjunction with the historic quad socket as with the relatively new, highly desirable, narrow, medial/lateral socket configuration.

It is another object of the present invention to provide an interface fitting module, as above, which eliminates the need for making a cast negative impression of the entire residual limb.

It is a further object of the present invention to provide an interface fitting module, as above, which virtually eliminates the need for making multiple socket checks.

It is still another object of the present invention to provide an interface fitting module, as above, which virtually eliminates both localized pressure points and gapping, resulting in a total contact socket.

It is yet another object of the present invention to provide an interface fitting module, as above, which may be fabricated from a material that can be selectively modeled with relative ease to conform to the configuration of the residual limb.

It is a still further object of the present invention to provide an interface fitting module, as above, which is preferably transparent in order to enable the prosthetist visually to detect blanching and gapping for precise modelling of the interface fitting module to the residual limb.

It is an additional object of the present invention to provide an interface fitting module, as above, which can be conveniently provided in several basic sizes, both right and left, for use with virtually all male and female patients, child or adult.

These and other objects of the invention, as well as the advantages thereof over existing and prior art forms, which will be apparent in view of the following detailed specification, are accomplished by means hereinafter described and claimed.

In general, an interface fitting module embodying the concepts of the present invention has a sleeve-like body portion. At least the proximal end of the sleeve-like body portion is open to receive a residual limb. Means are provided selectively to adjust the peripheral dimension of the body portion so that it will circumscribe, and engage, a residual limb. The body portion of the module is sufficiently transparent to permit visual observation as to the conformity of the module to the residual limb received therein. The material from which the body portion is fabricated is selected to permit modelling of the module as necessary to effect localized conformity of the module to the configuration of the residual limb received therein.

One exemplary interface fitting module, deemed sufficient to effect a full disclosure of the subject invention, is shown by way of example in the accompanying drawings and is described in detail without attempting to show all of the various forms and modifications in which the invention might be embodied; the invention being measured by the appended claims and not by the details of the specification.

BRIEF DESCRIPTION OF THE DRAWINGS

FIG. 1 is a generally anterior/medial perspective view which depicts an interface fitting module embodying the concepts of the present invention and adapted to be used in forming a socket for attaching a prosthetic limb to the right, residual thigh of an above-knee amputee;

FIG. 2 is an anterior, elevational view of the interface fitting module depicted in FIG. 1;

FIG. 3 is a proximal, plan view of the interface fitting module taken substantially along the line 3—3 of FIG. 2;

FIG. 4 is an anterior, elevational view of the interface fitting module depicted the previous views, represented as being fitted to the right, residual thigh of an above-knee amputee; and, FIG. 5 is an lateral, elevational view taken substantially along the line 5—5 of FIG. 4.

DESCRIPTION OF AN EXEMPLARY EMBODIMENT

One representative form of an interface fitting module embodying the concepts of the present invention is designated generally by the numeral 10 on the accompanying drawings. The representative interface fitting module 10 is preferably fabricated with a sleeve-like body portion 11 having open proximal and distal ends 12 and 13, respectively. The body portion 11 of the module 10 also tapers progressively from the proximal end 12 to the distal end 13 such that the peripheral dimension of the body portion 11 is normally greater at the proximal end 12 than it is at the distal end 13. An amputee's residual thigh 15 (FIGS. 4 and 5) may be insertably received through open, proximal end 12 of the module 10.

In order to accommodate the residual thigh 15 in the desired manner, the body portion 11 of the module 10 has a posterior wall 16 which merges into opposed medial and lateral walls 18 and 19, respectively. The medial wall 18, in turn, merges into an anterior wall 20. The lateral wall 19 merges into, and terminates as, an extension 22 which is disposed generally parallel to the anterior wall 20. In fact, the extension 22 and the anterior wall 20 are disposed in overlapping relation to form a lap joint 25.

The overlapping relation of the extension 22 and the anterior wall 20 thereby also effects a peripheral discontinuity 26 which extends the full longitudinal length of the body portion 11. That is, the discontinuity 26 extends from the proximal end 12 through the distal end 13 of the body portion 11. The discontinuity 26 permits the peripheral dimension of the body portion 11 to be adjusted by sliding the contiguously juxtaposed, and overlapping, extension 22 and the anterior wall 20 in whatever direction is required to vary the extent to which they overlap. The extent of the overlap can also be progressively varied, to some degree, between the proximal and distal ends 12 and 13, respectively, in order to accommodate the particular "conicity" of the residual thigh 15 received therein.

The body portion 11 of the module 10 is provided with a brim 28, which forms a seat that underlies, and supports, the patient's ischial tuberosity. Specifically, the proximal end portions of the posterior wall 16 and the medial wall 18, at least in proximity to the juncture of those walls, terminate in the brim 28 which extends generally outwardly from the proximal ends of the adjacent posterior and medial walls 16 and 18, respectively. It is important that the ischium receive proper support, because the amputee's weight will be transferred through the ischium to the interface when the patient is wearing the actual prosthesis. It is the brim 28 which provides the desired support to the ischium, as well as comfort to the wearer.

The longitudinal dimension of the body portion 11 is such that the distal end 13 of the module 10 will be located beyond the distal end 29 of the residual thigh 15.

The interface fitting module 10 may be molded from a transparent, polymeric, thermoplastic material. As is hereinafter discussed in considerably greater detail relative to the explanation as to the fitting of the module 10 to the patient's residual thigh 15, visual examination, and observation, of the residual thigh as it is received within the module 10 greatly facilitates determining the necessary adjustments which are, in turn, readily imparted to the module by virtue of its thermoplastic composition. One particularly suitable thermoplastic material for fabrication of the module 10 is the ionomer family of resins commercially available under the brand name SURLYN. SURLYN is a registered trademark of E.I. DuPont de Nemours & Co. Of course, it must be understood that the present invention is in no way limited to the use of any particular resin.

It is envisioned that the module 10 may be initially made in three general sizes, such as small, medium and large, both right and left. To fit a particular amputee, a module 10 is selected which is approximately the same circumferential dimension as the amputee's residual thigh 15. The module 10 is then exactly fitted to the amputee as hereinafter more fully described.

Lotion is applied to the skin of the patient's residual thigh 15 in order to facilitate insertion of the residual thigh 15 into the module 10. Before the module 10 is donned, however, the circumferential dimension of the residual thigh 15 is measured at a plurality of longitudinally spaced locations along its length. Those dimensions are recorded, and the locations where the measurements were taken are marked directly upon the skin of the patient's residual thigh. Vertical reference lines are also applied to at least the anterior and lateral surfaces of the residual thigh 15.

The prosthetist transfers the circumferential measurements of the residual thigh to the outside of the module 10, and by manipulating the lap joint 25 the circumferences of the module 10 at several locations along the length thereof are brought into conformity with the circumferences of the residual thigh at corresponding longitudinal locations, even before the patient dons the module 10. Strips 30 of tape are applied across the lap joint 25 temporarily to secure the adjusted circumferences of the module 10.

The residual thigh 15 is then inserted through the open, proximal end 12 of the module 10. When the residual thigh 15 is insertably received therein it will rest against the posterior wall 16 of the module 10, with the medial, lateral and anterior walls 18, 19 and 20, respectively, embracing the corresponding surfaces on the residual thigh 15. The distal end 13 of the module 10 is placed on a support, such as a stool, so that the amputee can stand upright with the interface fitting module 10 containing the residual thigh 15 and bearing the appropriate share of the amputee's weight.

The prosthetist then performs a visual examination of the residual thigh 15 through the transparent body portion 11 of the module 10 to be certain that there are no rolls of flesh formed at the proximal brim 28 and that there are no red or white areas of skin. If necessary, the relative disposition of the extension 22 and the anterior wall 20 may be manipulated, by virtue of the lap joint 25, to effect a more exacting circumferential engagement of the body portion 11 with the residual thigh 15. When the desired circumferential engagement of the module 10 to the residual thigh 15 has been achieved, the disposition of the lap joint 25 may be re-secured by the strips 30 of tape, as depicted in FIGS. 4 and 5.

All circumferential measurement marks 31, and vertical reference lines 32 marked on the skin are then traced onto the exterior of the module 10, and an extra wrap 33, or two, of tape may be applied to assure that the lap joint 25 will remain secured.

The module 10 is then removed, and perhaps three longitudinally spaced bores 34 are drilled through the overlapping extension 22 and anterior wall 20 to receive two-piece screws, or threaded rivets, 35 by which permanently to secure the relative disposition of the extension 22 and that portion of the anterior wall 20 which forms the lap joint 25. Thereafter, the strips 30, and wraps 33, of tape are removed to allow unobstructed visual observation of the residual thigh 15 through the body portion 11 of the module 10, and the patient reinserts the residual thigh 15 into the module 10.

Once again the patient applies an appropriate portion of his, or her, weight to the module 10 and the prosthetist is able to see through the transparent interface fitting module 10 to observe the amputee's residual thigh 15. The skin is palpated to identify localized areas of the module 10 which too tightly, or too loosely, engage the residual thigh 15. Those localized areas are marked directly on the walls of the module 10. The module 10 is then removed from the residual thigh 15, and by use of an ordinary hot air gun, the module 10 is heated at the areas previously marked. When sufficiently heated and pliable, the walls of the module 10 may be modelled as required to correct the ill-fitting areas which the prosthetist marked. The module is repeatedly replaced onto the residual thigh 15, and marked, heated and modelled until a proper fit is obtained. The brim 28 may also be heated and modelled in order to provide an exact, weight bearing seat for the amputee's ischial tuberosity.

Once the module 10 has been properly fitted to the residual thigh 15, the module is circumferentially marked as at 36 (FIGS. 4 and 5), to identify the location at which the distal end 29 of the residual thigh ceases to contact the module 10. Thereafter, the module 10 is removed from the patient, and a plurality of relief bores 38 are drilled slightly proximal of the circumferential line 36 which identifies loss of contact between the residual thigh 15 and the module 10. The relief bores 38 are blocked with tape 39, and the distal end 13 of the body portion 11 is closed, as by taping, not shown. An impression material 40, such as an alginate mixture, is poured into the module 10 in order to fill the module to a point just proximal to the level of the line 36 which designates the location at which the distal end 29 of the residual thigh 15 would be located if it were in the module 10.

The residual thigh 15 is once again inserted into the module 10, and the amputee applies his, or her, body weight to the supported module 10 so as to force the distal end 29 of the residual thigh 15 into the impression material 40. Air and excess impression material 40 are permitted to escape through the relief bores 38, and the relief bores 38 are reblocked by tape 39 until the impression material 40 is sufficiently set so that the residual thigh 15 can be removed, leaving an impression of the distal end 29 of the residual thigh 15.

The resulting module 10, including the impression of the distal end 29 of the residual thigh 15, is an exact negative model of the residual thigh 15 in the configuration it assumes when bearing the amputee's weight. A positive casting of the residual thigh 15 made from the finished module 10 permits the interface portion of a prosthetic socket to be fabricated to the exact configuration of the residual thigh 15 the first time. The interface of the resulting socket thus provides maximum support to the ischial tuberosity and maximum of comfort for the amputee.

As should now be apparent, the present invention not only provides an improved article and method by which to fit the interface of a prosthetic socket employed to secure an artificial limb to the residual thigh of an above-knee amputee but also accomplishes the other objects of the present invention.

I claim:

1. A method for fitting the interface portion of an ischial containment socket to the residual limb of an above-knee amputee comprising the steps of:
   providing a hollow, transparent, thermoplastic, sleeve-like interface fitting module that has a peripheral discontinuity which extends between the proximal and the distal ends of the module;
   inserting a residual limb through the proximal end of the module into the hollow interior thereof;
   adjusting the peripheral dimension of the module to bring it into general conformity with the configuration of the residual limb received therein;
   securing the adjusted peripheral dimension of the module;
   marking those localized areas on the module which blanch the skin of, or gap away from, the residual limb received therein;
   removing the residual limb from the module;
   heating the marked, localized areas of the module;
   modelling the heated areas of the module to bring them into the desired engagement with the residual limb; and,
   repeating the previous three steps, as required.

2. A method for fitting a module, as set forth an claim 1, comprising the additional steps of:
   manually manipulating the distal end of the residual limb, through the open distal end of the module, as required to dispose the residual limb within the module.

3. A method for fitting a module, as set forth an claim 2, comprising the additional steps of:
   closing the distal end of the module;
   inserting a molding material within the module; and,
   casting the configuration of the distal end of the residual limb in situ within the module.

4. A method for fitting a module, as set forth in claim 3, comprising the additional steps of:
   removing the residual limb from the module after the casting of the distal end of the residual limb has hardened;
   employing the negative impression of the residual limb formed by the module and the casting contained therein to cast an accurate, positive impression of the residual limb from which to fabricate the interface of an ischial containment socket.

* * * * *